United States Patent [19]
Jack et al.

[11] Patent Number: 5,831,267
[45] Date of Patent: Nov. 3, 1998

[54] METHOD AND APPARATUS FOR REMOTE MEASUREMENT OF EXHAUST GAS

[75] Inventors: Michael D. Jack; Jay C. Peterson, both of Goleta; David R. Nelson; Michael N. Gray, both of Santa Barbara, all of Calif.

[73] Assignee: Envirotest Systems Corp., Sunnyvale, Calif.

[21] Appl. No.: 806,870

[22] Filed: Feb. 24, 1997

[51] Int. Cl.$^6$ ............................................ G01N 21/31
[52] U.S. Cl. ............................ 250/338.5; 250/339.13; 250/372
[58] Field of Search .................. 250/338.5, 339.13, 250/372

[56] References Cited

U.S. PATENT DOCUMENTS

| | | | |
|---|---|---|---|
| 2,930,893 | 3/1960 | Carpenter et al. | 250/43.5 |
| 3,171,027 | 2/1965 | Wallack | 250/83.3 |
| 3,287,556 | 11/1966 | Good | 250/43.5 |
| 3,364,351 | 1/1968 | Palmer et al. | 250/43.5 |
| 3,696,247 | 10/1972 | McIntosh et al. | 250/83.3 H |
| 3,958,122 | 5/1976 | Jowett et al. | 250/346 |
| 3,973,848 | 8/1976 | Jowett et al. | 356/51 |
| 4,126,396 | 11/1978 | Hartmann et al. | 356/434 |
| 4,160,373 | 7/1979 | Fastaia et al. | 73/23 |
| 4,204,768 | 5/1980 | N'Guyen | 356/243 |
| 4,348,732 | 9/1982 | Kreft | 364/571 |
| 4,390,785 | 6/1983 | Faulhaber et al. | 250/330 |
| 4,490,845 | 12/1984 | Steinbruegge et al. | 382/1 |
| 4,632,563 | 12/1986 | Lord, III | 356/437 |
| 4,678,914 | 7/1987 | Melrose et al. | 250/343 |
| 4,746,218 | 5/1988 | Lord, III | 356/437 |
| 4,755,678 | 7/1988 | Izatt et al. | 250/358.1 |
| 4,795,253 | 1/1989 | Sandridge et al. | 356/51 |
| 4,818,705 | 4/1989 | Schneider et al. | 436/164 |
| 4,914,719 | 4/1990 | Conlon et al. | 250/339 |
| 4,924,095 | 5/1990 | Swanson, Jr. | 250/338.5 |
| 4,963,023 | 10/1990 | Goldovsky et al. | 356/308 |

(List continued on next page.)

FOREIGN PATENT DOCUMENTS 54-5778   1/1979   Japan .

OTHER PUBLICATIONS

Menzies et al., Remote measurement of ambient air pollutants with a bistatic laser system, applied Physics, vol. 15, No. 9, pp. 2080–2084, Sep. 1976.

Lowell L. Ashbaugh, et al., Presented at AWMA/EPA Conference on "PM$_{10}$ Standards and Nontraditional Particulate Source Controls," Jan. 1992, On–Road Remote Sensing of Carbon Monoxide and Hydrocarbon Emissions During Several Vehicle Operating Conditions.

Lowell L. Ashbaugh et al., Presented at AWMA Specialty Conference, abstract of session on "Non–Traditional Approaches to Motor Vehicle Emissions and Controls", No Date.

Thomas C. Austin et al., "An Evaluation of 'Remote Sensing' For The Measurement of Vehicle Emissions," Aug. 1990, pp. 1–31.

Gary A. Bishop et al., American Chemical Society, 1989, "IR Long–Path Photometry: A Remote Sensing Tool For Automobile Emissions," pp. 671A–676A.

(List continued on next page.)

*Primary Examiner*—David P. Porta
*Attorney, Agent, or Firm*—Hunton & Williams

[57] ABSTRACT

A method and apparatus for sensing a composition of an exhaust plume includes a light source that radiates an infrared light beam having a plurality of predetermined wavelengths. A first of the predetermined wavelengths is associated with carbon dioxide and a second of the predetermined wavelengths is associated with a second gas, such as a hydrocarbon or carbon monoxide. The apparatus also includes a detector unit that detects the beam passing through the plume. The apparatus computes a ratio of the second gas to carbon dioxide based upon the first and second detected wavelengths, and this ratio is then multiplied by a predetermined estimation of a concentration of carbon dioxide in the plume.

24 Claims, 1 Drawing Sheet

U.S. PATENT DOCUMENTS

| | | | |
|---|---|---|---|
| 4,999,498 | 3/1991 | Hunt et al. | 250/338.5 |
| 5,002,391 | 3/1991 | Wolfrum et al. | 356/307 |
| 5,041,723 | 8/1991 | Ishida et al. | 250/339 |
| 5,061,854 | 10/1991 | Kroutil et al. | 250/339 |
| 5,076,699 | 12/1991 | Ryan et al. | 356/437 |
| 5,210,702 | 5/1993 | Bishop et al. | 364/496 |
| 5,319,199 | 6/1994 | Stedman et al. | 250/338.5 |
| 5,371,367 | 12/1994 | DiDomenico et al. | 250/338.5 |
| 5,373,160 | 12/1994 | Taylor | 250/338.5 |
| 5,401,967 | 3/1995 | Stedman et al. | 250/338.5 |
| 5,418,366 | 5/1995 | Rubin et al. | 250/338.5 |
| 5,498,872 | 3/1996 | Stedman et al. | 250/338.5 |
| 5,591,975 | 1/1997 | Jack et al. | 250/338.5 |
| 5,621,166 | 4/1997 | Butler | 250/338.5 X |

OTHER PUBLICATIONS

Gary A. Bishop et al., Society of Automotive Engineers, Inc., 1989, "Oxygenated Fuels, A Remote Sensing Evaluation," pp. 1–8.

Lucian W. Chaney, Journal of the Air Pollution Control Association, Mar. 1983, vol. 33, No. 3, "The Remote Measurement of Traffic Generated Carbon Monoxide," pp. 220–222.

Paul L. Guenther et al., American Petroleum Institute, Jun. 1991, "Remote Sensing of Automobile Exhaust".

John B. Heywood, Internal Combustion Engine Fundamentals, 1988, Chapter 3, "Thermochemistry of Fuel–Air Mixtures," pp. 62–97.

John B. Heywood, Internal Combustion Engine Fundamentals, 1988, Chapter 4.9, "Properties of Working Fluids," pp. 145–155.

John B. Heywood, Internal Combustion Engine Fundamental, 1988, Chapter 11, "Pollutant Formation and Control," pp. 567–625.

Douglas R. Lawson et al., Air & Waste Management Association, vol. 40, No. 8, Aug. 1990, "Emissions from In–Use Motor Vehicles in Los Angeles: A Pilot Study of Remote Sensing and the Inspection and Maintenance Program," pp. 1096–1105.

James E. Peterson et al., Chemtech, Jan. 1992, "Find and Fix the Polluters," pp. 47–53.

Brett C. Singer et al., Journal of the Air & Waste Management Association, vol. 46, Jun. 1996, "A Fuel–Based Motor Vehicle Emission Inventory," pp. 581–593.

Donald H. Stedman, Environmental Science & Technology, 1989, vol. 23, No. 2, "Automobile Carbon Monoxide Emission," pp. 147–149.

Donald H. Stedman, "Science and Politics of Air Pollution From Cars," Mar. 1995, pp. 1–11.

Donald H. Stedman et al., Illinois Dept. of Energy and Natural Resources, Mar. 1990, "An Analysis of On–Road Remote Sensing as a Tool for Automobile Emissions Control".

Donald H. Stedman et al., Report to California Air Resources Board, "On–Road Remote Sensing of CO and HC Emissions in California", No Date.

Robert D. Stephens, et al., Air & Waste Management Association, vol. 41, No 1, Jan. 1991, "Remote Sensing Measurements of Carbon Monoxide Emissions from On–Road Vehicles," pp. 39–46.

Robert D. Stephens, Journal of Air & Waste Management Association, vol. 44, Nov. 1994, "Remote Sensng Data and a Potential Model of Vehicle Exhaust Emissions," pp. 1284–1292.

Robert D. Stephens et al., General Motors Research Laboratories, for presentation to Air Waste Management Association, May 1990, "Remote Sensing of Carbon Monoxide Emissions from On–Road Vehicles," pp. 1–45.

Robert D. Stephens et al., General Motors Research Laboratories, for presentation to Society of Automotive Engineers Government/Industry Meeting, May 15, 1991, "Remote Sensing Measurements of In–Use Vehicle Carbon Monoxide and Hydrocarbon Exhaust Emissions," pp. 1–9.

Yl Zhang, Environmental Science and Technology, vol. xx, vol. No xx, xxxx, "On–Road Hydrocarbon Remote Sensing in the Denver Area" no date.

Progress Report, Real–World Emissions, Feb. 1, 1991.

Progress Report, Real–World Emissions, Apr. 2, 1991.

Progress Report, Real–World Emissions, Jun. 1, 1991.

Real–World Emissions, Jul. 1, 1991.

Progress Report, Real–World Emissions, Oct. 1, 1991.

LEXIS Printout of Environmental Protection Agency, 40 CFR Part 51, Inspection/Maintenance Program Requirements, Nov. 5, 1992, pp. 3–43.

METHOD AND APPARATUS FOR REMOTE MEASUREMENT OF EXHAUST GAS

BACKGROUND OF THE INVENTION (a) Field of the Invention

The present invention relates generally to the monitoring of environmental pollution, and more specifically to a system for the remote sensing of gaseous exhaust compositions, such as those produced by motor vehicles.

(b) Description of Related Art

Environmental pollution, such as air pollution, is a serious problem that is particularly acute in urban areas. Much of this pollution is produced by exhaust emissions from motor vehicles. Governmental standards have been set for regulating the allowable amounts of certain pollutants in automobile exhausts, and in many areas periodic inspections are required in order to ensure that vehicles meet these standards.

For example, many states have initiated mandatory periodic inspection and maintenance (I/M) procedures during which the pollutants in the vehicle exhaust are monitored and compared with predetermined standards. If the vehicle emissions fail to meet these standards, the vehicle generally must be repaired so that emission standards are met.

Nevertheless, there are still large numbers of vehicles operating on public roads that fail to comply with the governmental standards. Highly polluting vehicles can operate even in areas in which periodic emission inspections are required. For example, some older vehicles and special types of vehicles can be exempt from inspections. In addition, where a substantial period of time is allowed to pass between the required periodic inspections, a vehicle's emission controls can malfunction.

Moreover, although anti-pollution devices that are required equipment on newer vehicles generally accomplish their intended purpose of reducing pollution in the vehicle exhaust to within prescribed levels, it is perceived by some vehicle owners that anti-pollution equipment reduces engine performance. For this reason, some vehicle owners have been known to perform whatever servicing is necessary to place their vehicles in condition to pass required inspections, and subsequently remove, adjust, and/or intentionally disable anti-pollution devices for normal use. Furthermore, it is believed that a disproportionately large amount of pollution is generated by a relatively small number of vehicles. Therefore, it would be advantageous to provide a system for testing vehicles that does not require owner participation.

Inspection programs typically use an idle test procedure that monitors vehicle emissions at idle speeds while the vehicle is stopped. Idle emission standards are typically set at limits sufficiently high to accommodate equipment errors, operator errors, and calibration errors. The result of this process is that many vehicles with faulty or substandard emission equipment can escape the test and maintenance requirements and continue to operate with high emissions that pollute the environment. The idle test procedures do not test the engine when it is run in a loaded mode, and the largest percentage of pollutants is produced either during the acceleration of a vehicle or when maintaining a constant velocity under load, rather than when in stationary idle. Thus, if the test procedure is run with a stationary vehicle, the transmission not engaged, and no load exerted on the engine, the check often does not accurately measure the engine pollutants during normal vehicle operation. A device is thus needed to measure the exhaust pollutants during a realistic operation period of the vehicle.

An anti-pollution program depending entirely on mandatory periodic inspections performed at fixed facilities can therefore be inadequate. It would be advantageous to identify vehicles that are actually operating in violation of prescribed emission standards, and either require them to be placed in conformance with the standards or be removed from operation.

A remote gas analyzer for motor vehicle exhaust testing is disclosed in U.S. Pat. No. 4,924,095 to Swanson, Jr., the disclosure of which is hereby incorporated herein by reference in its entirety. One embodiment of the disclosed system utilizes absorption spectroscopy to determine the amount per unit volume of pollutants in an exhaust plume from a motor vehicle. A first plurality of optical beams is arranged to form a first array of beams encompassing substantially an entire cross-section of an exhaust plume along a predetermined length of the exhaust plume.

The spectral content of the first plurality of beams is analyzed in order to determine the concentration in the exhaust plume of a first preselected pollutant, typically carbon monoxide or carbon dioxide. A computer determines the relative increase in the amount per unit volume of the first pollutant caused by the motor vehicle. A second gas analyzer includes a second beam intersecting the exhaust plume to allow determination of the increase in concentration of a plurality of pollutants, one of which is the aforementioned first pollutant. The computer further determines the relative increase in the amount per unit volume of a second pollutant gas (i.e., other than the pollutant measured by the array of beams) by using the ratio of the increased amount of the second pollutant to the increased amount of the first pollutant. This ratio is multiplied by the relative increase in the concentration of said first pollutant gas (measured by the array) to determine the amount per unit volume of the second gas. However, this system has the disadvantage in that it requires an array of beams monitoring a space sufficiently large to contain a total cross-section of an exhaust plume. It would be advantageous to provide a system that does not require, among other things, an array of beams to measure the concentration of pollutants in an exhaust plume.

Another apparatus for remote analysis of vehicle emissions is disclosed in U.S. Pat. No. 5,498,872 to Stedman et al., the disclosure of which is hereby incorporated herein by reference in its entirety. The disclosed apparatus utilizes stoichiometric ratios applicable to a general combustion reaction in order to approximate relative amounts of individual emission components, as opposed to using a full array of beams (as in Swanson) to obtain a measure of the total amount of pollutants emitted in an exhaust plume. The disclosed method of Stedman, however, has the disadvantage, for example, of apparently relying on the erroneous assumption that the exhaust and fuel have the same hydrocarbon composition. In addition, the disclosed method contemplates the need for an ultraviolet radiation source for the measurement of $NO_x$ pollutants. It would be advantageous to provide a method that does not require such an assumption and that does not require a source of ultraviolet radiation to measure $NO_x$ pollutants.

Another apparatus for remote analysis of vehicle emissions is disclosed in U.S. Pat. No. 5,591,975 to Jack et al., which is assigned to the assignee of the present application and is also hereby incorporated herein by reference in its entirety.

SUMMARY OF THE INVENTION

This invention is directed to a method and apparatus for sensing the composition of an exhaust plume, such as that produced by a moving motor vehicle. A light source radiates an infrared light beam having a plurality of predetermined wavelengths through an exhaust plume of a motor vehicle. The system also includes a detector that detects the beam passing through the plume at the predetermined wavelengths. A first of the predetermined wavelengths is associated with carbon dioxide and a second of the predetermined wavelengths is associated with a second gas, such as hydrocarbon gases. The apparatus computes a ratio of the second gas to carbon dioxide based upon the first and second detected wavelengths. This ratio is multiplied by a predetermined estimation of a concentration of carbon dioxide in the plume.

The invention also provides a method and apparatus for determining the content of nitrogen oxides in an exhaust stream through the use of an infrared radiation source. The method includes determining a ratio of nitrogen oxide to carbon dioxide and multiplying this ratio by a predetermined estimation of the concentration of carbon dioxide in the exhaust stream.

The invention itself, together with further objects and attendant advantages, will best be understood by reference to the following detailed description, taken in conjunction with the accompanying drawing.

BRIEF DESCRIPTION OF THE DRAWING

The sole figure is a schematic diagram of an embodiment of a remote exhaust measurement system of the invention.

DETAILED DESCRIPTION OF PREFERRED EMBODIMENTS

Figure 1:
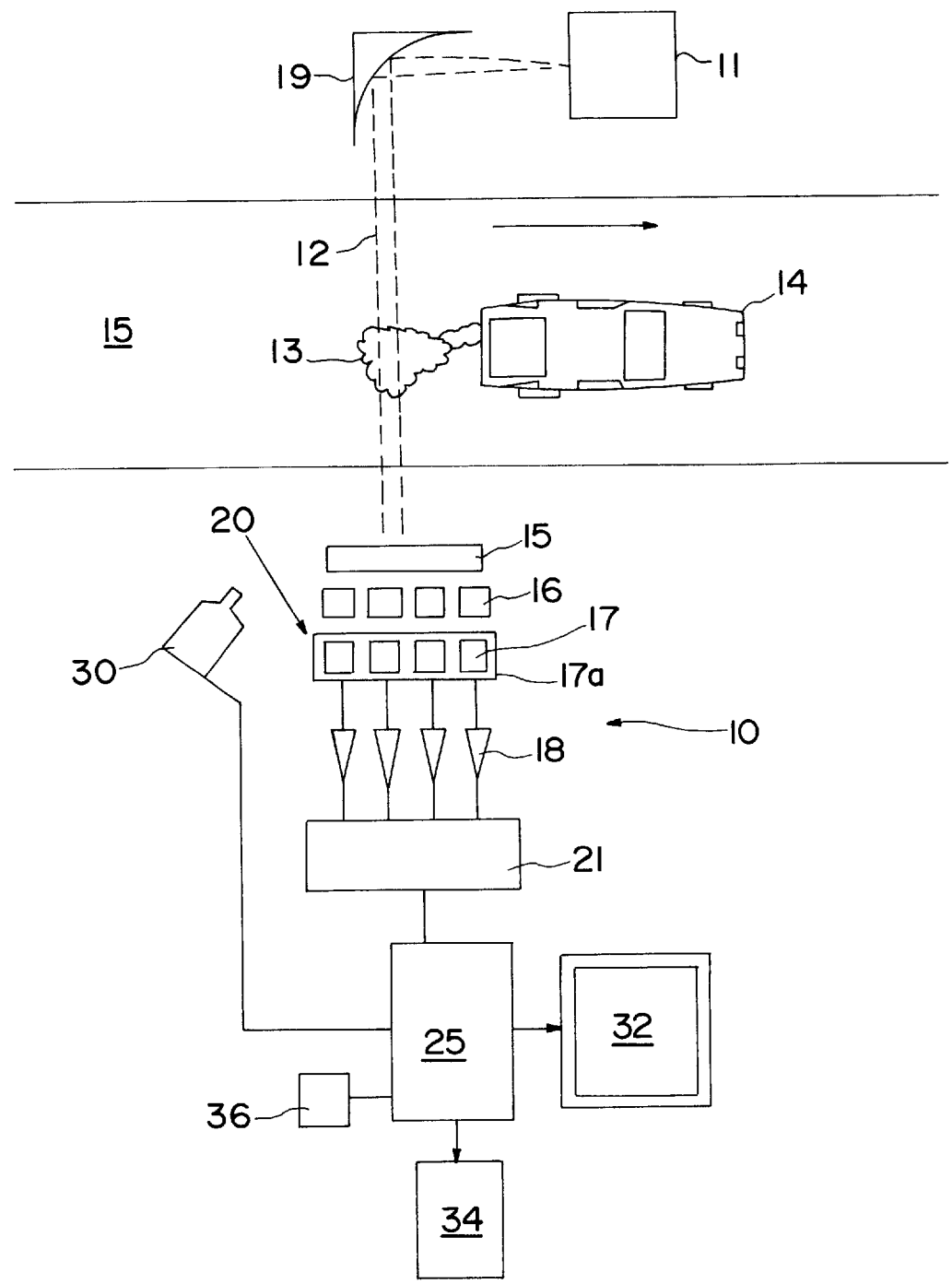

The invention provides a method and system for measuring the composition of an exhaust gas produced by one of the various sources discussed below, for example, the engine of a motor vehicle.

Generally, the system of the invention measures the concentrations of pollutant gases emitted in exhaust streams, for example in the exhaust plume of a moving motor vehicle, by analyzing the infrared absorption at selected frequencies of a sample of the exhaust plume. The specific frequencies selected in the infrared range correspond to various pollutants of interest, which typically include carbon monoxide, carbon dioxide, hydrocarbons, and oxides of nitrogen such as nitrogen oxide. The infrared absorption data can be analyzed as described below to provide the approximate concentrations of the pollutants in the exhaust.

Discussed in detail below is a system for measuring the composition of exhaust gas from a motor vehicle that emits an exhaust plume as the vehicle travels along a roadway. However the invention is not limited to measurement of exhaust from motor vehicles, but can also be used to measure emissions from many other sources, including those where the source of the exhaust is not moving. Preferably, however, the invention is used to measure the composition of an exhaust stream or plume produced by a motor vehicle having an internal combustion engine. Such exhaust plumes typically include carbon dioxide ($CO_2$), carbon monoxide (CO), hydrocarbons (HC or CH), water vapor ($H_2O$), and nitrogen oxide (NO), for example.

Referring the figure, the system (referred to generally as element 10) includes a source 11 for supplying infrared ("IR") radiation. The source 11 is preferably a broad band IR source, for example a source having a silicon carbide filament with an associated power supply, and has the ability to produce significant IR radiation in the range of about three micrometers to about six micrometers, for example. The infrared radiation source 11 provides a beam 12 that may optionally be passed through a chopper (not shown), as discussed in U.S. Pat. No. 5,591,975. The infrared radiation source 11 may be associated with a beam former 19, such as a parabolic reflector, for example.

The beam 12 is aligned so that it passes through an exhaust gas plume 13 of a vehicle 14 when the vehicle 14 is in motion on a roadway 15 in the direction indicated in the figure. The passage of the IR beam 12 through the exhaust gas plume 13 results in the selective partial absorption of various wavelengths within the broad band beam, the selective absorption occurring because of the presence of $NO_X$, water vapor, $CO_2$, CO, HC (hydrocarbons), and other species within the exhaust gas. As is known by those of skill in the art, each of the aforementioned species absorbs infrared radiation at or near a known wavelength or wavelengths.

After passing through the plume 13, the beam 12 may pass through an optional IR-transparent gas cell (not shown) used for calibration purposes, and then through a beam integrator or diffuser 15. The diffused beam is applied to a plurality of narrow band filters 16, each of the filters corresponding to a measurement channel. Each filter 16 is selected so as to pass a predetermined narrow band of wavelengths to a focal plane 17a having a plurality of photodetectors 17 individually tuned for a specific pollutant. A detector unit including the focal plane 17a is referred to generally as element 20. Each photodetector 17 outputs an electrical signal to an input of a corresponding measurement channel including suitable analog electronics (represented by element 18), an analog-to-digital converter 21, and a data processor 25 having one or more associated output devices described below.

The data processor 25 provides the required signal processing of the outputs from the analog-to-digital converter 21. The data processor 25 can be coupled to a lookup table, which is most readily implemented as a region of memory (semiconductor and/or disk) accessible by the data processor 25, as described in U.S. Pat. No. 5,591,975 (previously mentioned) and in U.S. Pat. No. 5,418,366, the disclosure of which is hereby incorporated herein by reference in its entirety. A suitable cooler, such as a thermo-electric device known to those of skill in the art, can be employed for cooling the IR detectors 17 which are typically required to be cooled to an operating temperature that is below ambient temperature.

There can be, for example, at least six spectral measurement channels, depending upon the number of pollutants and reference channels that are desired to be monitored. For example, there can be an NO spectral channel (having a filter with a pass band centered on about 5.26 micrometers), an $H_2O$ spectral channel (having a filter with a pass band centered on about 5.02 micrometers), a first reference, or $CO_2$, spectral channel (having a filter with a pass band centered on about 4.2 micrometers), a CO spectral channel (having a filter with a pass band centered on about 4.6 micrometers), an HC spectral channel (having a filter with a pass band centered on about 3.3 micrometers), and a second reference spectral channel having a filter with a pass band centered on about 3.8 micrometers. Additional channels to measure other pollutants can also be added if desired. Those of skill in the art will know how to select suitable measurement and reference channels.

The light source 11 sends a beam of radiation 12 into the detector unit 20 on a continuous basis. The data processor 25 continuously samples all beam intensities received by each of the detector 17 of the detector unit 20. In addition, when the beam 12 is blocked by a vehicle 14 as it passes along the roadway 15, the data processor 25 retains information concerning the carbon monoxide, carbon dioxide, hydrocarbon, nitrogen oxides, and/or water levels in the ambient atmosphere in front of the vehicle 14 prior to the blocking of the beam. This will provide a measurement of "background pollution" so as to exclude ambient or background levels of pollution from measurement as exhaust pollution of the vehicle 14. The analysis of the data provided by the system 10 will exclude this background level of pollution.

Subsequently, the detector unit 20 and data processor 25 cooperate to sample the carbon monoxide, carbon dioxide, hydrocarbon, nitrogen oxides, and water levels (or others depending upon desired monitoring) of the exhaust plume 13 trailing the vehicle 14 for a predetermined period after resumption of reception of the beam by the detector unit 20. This predetermined sampling period is generally about 0.1 second to about 1.0 second, for example about one-half second. The system 10 can then reset for the next passing vehicle.

A reference channel is preferably used in order to remove fluctuations in IR absorption due to the presence of particulate material. The raw signal obtained after the arrival of the vehicle 14 in the test area (the samples described above) is divided by the signal prior to the arrival of the vehicle. This mechanism is described in U.S. Pat. No. 5,591,975.

Preferably, the system includes apparatus for identifying the vehicle 14 when desired, such as when the vehicle 14 exhibits unacceptable levels of emissions. A video camera 30 can record an end view of the vehicle 14 and the vehicle's license plate simultaneously with the unblocking of the beam by the vehicle 14 (or at some other time after the vehicle passes through the beam). Alternatively, the front or other portions of the vehicle 14 can be recorded. After the sampling and analysis is performed as described herein, the levels of various pollutants (e.g., CO, $CO_2$, HC, $NO_x$, and water) can be displayed and/or permanently stored via an associated output device, along with any other identifying information such as date and time of the test. Preferably, this information is permanently stored magnetically or electronically, although any type of storage can be utilized with the invention, including digital image storage. The information can be displayed on an output monitor 32 and/or stored in a video recorder 34. The information can also be stored in an electronic memory device 36.

The system 10 can be designed to itself read the vehicle license plate using optical character recognition software known to those of skill in the art. In this manner, the need for manual identification can be eliminated or reduced. The data can be retrieved at a later time for enforcement use, such as sending a notice of violation (or a notice requiring manual inspection of the vehicle) to the owner of the vehicle 14. Alternatively, an operator of the system may read the recorded information from the monitor 32 and subsequently input the information and license plate number manually into a computer database. The system can also store combined video and data information for every vehicle that is tested, rather than for just excessively polluting vehicles, for applications such as the generation of a database of exhaust gas composition for different types and models of vehicles.

In operation, the detector unit 20 is preferably set up along the single-lane roadway 15 with the beam located about 8 inches to 12 inches, for example 10 inches, above the roadway 15. The above-described data processor 25 monitors the intensity of the signal channels described above.

When the vehicle 14 enters into the optical path of the beam 12, a drop in voltage signals the presence of the vehicle 14. Voltages from each of the signal channels (e.g., the detector for NO, CO, $CO_2$, HC, and $H_2O$) that were acquired prior to the interruption of the beam 12 by the vehicle 14 are stored in the data processor 25. After the vehicle 14 exits the beam path so that the beam 12 is again received by the detector unit 20, the data processor 25 once again begins to acquire a stream of voltage samples from each of the detector over time. The detector unit 20 and data processor 25 continue to sample voltages from each of the detectors 17 for the aforementioned sampling period of about 0.1 second to about 1.0 second after the vehicle 14 exits the beam path. Preferably, the signals from the detectors are averaged by the data processor 25 over a period of about 1 millisecond to about 20 milliseconds for each sample. In this manner, a more accurate signal-to-noise ratio can be obtained.

The analysis performed by the data processor 25 will now be described in more detail. As mentioned above, the data processor 25 is able to compute the amounts of pollutants present in the exhaust plume 13 based in part (but only in part) upon relative amounts of pollutants observed in the exhaust by the infrared sampling mechanism. Initially, as mentioned above, voltage data as a function of time is accumulated from a hydrocarbon detector, a carbon monoxide detector, a carbon dioxide detector, a nitrogen oxide detector, and a reference detector, for example.

After the apparatus measures the difference between (a) the transmission value of a pollutant present before the vehicle 14 passes through the test area and (b) the transmission value of the pollutant in the plume 13, these raw data are preferably normalized. For example, the ratios of the CO voltages to reference voltages are computed, and these arbitrary units are rescaled into calibrated CO values. As described in U.S. Pat. Nos. 5,591,975 and 5,418,366, a polynomial equation is preferably used to convert the raw data into an effective concentration (in percent or parts per million) of the detected pollutants.

Carbon Monoxide Measurement

Measurement of the carbon monoxide content of a vehicle can initially include a determination of a correlation between the concentration of hydrocarbons (HC) and carbon dioxide ($CO_2$). This correlation can be obtained, for example, by plotting in a correlation graph the HC and $CO_2$ values obtained by the data processor 25 via the detectors 17. The data processor 25 calculates the slope of an optimal line corresponding to these values by a least-squares regression analysis. The slope of this line is the HC:$CO_2$ molar ratio (also referred to herein as $R_{HC/CO2}$ or HC/$CO_2$), and it represents the measurement of the relative molar amounts of hydrocarbons and carbon dioxide in the exhaust plume. This analysis is also described in U.S. Pat. No. 5,418,366.

Similarly, a correlation between the concentration of carbon monoxide (CO) and carbon dioxide ($CO_2$) is also determined. Similar to the calculation for $R_{HC/CO2}$ above, a correlation between CO and $CO_2$ can be obtained, for example, by plotting in a correlation graph the CO and $CO_2$ values obtained by the data processor 25 via the detectors 17. The data processor 25 calculates the slope of an optimal line corresponding to these values by a least-squares regression analysis. The slope of this line is the CO:$CO_2$ molar ratio (also referred to as $R_{CO/CO2}$ or CO/$CO_2$), and it represents the measurement of the relative molar amounts of carbon monoxide and carbon dioxide in the exhaust plume.

The values for $R_{CO/CO2}$ and $R_{HC/CO2}$ are utilized in a calculation of an estimated concentration of carbon monoxide in the exhaust plume. More specifically, in order to provide the concentration of carbon monoxide, the values for $R_{CO/CO2}$ and $R_{HC/CO2}$ are preferably utilized in a calculation that incorporates relative amounts of components of a fuel combustion reaction. The calculation, such as that represented in equations 27, 23, and 30 below, incorporates differing assumptions of hydrocarbon contents of the fuel and the exhaust. A derivation of equations 23 and 27 will now be illustrated.

An internal combustion engine burns a fuel containing carbon and hydrogen (formula $CH_x$) with air, wherein the approximate formula for air can be considered as 0.21 $[O_2]$+0.79 [IATM], wherein "IATM" is the inert atmospheric gas concentration. Nitrogen is the major component of IATM. Thus, n moles of $O_2$ require 3.76 n moles of inert constituents of atmosphere by volume.

The combustion process can be described by the equation below, where "$R_{HCF}$" is the H:C ratio for fuel and "$R_{HC}$" is the H:C ratio for the exhaust.

$$[CH_{R_{HCF}}] + n[O_2] + 3.76\, n[IATM] = k[CO_2] + 1[CO] + m[CH_{R_{HC}}] + k'[H_2O] + 3.76\, n[IATM] \quad (1)$$

In the discussion below, the H:C ratio for fuel ($R_{HCF}$) will later be assumed to be about 1.85, since as a simplifying generalization, it is assumed that in the fuel there are equal concentrations of alkanes, alkenes, and aromatics in the forms $C_8H_{18}$, $C_8H_{16}$, and $C_6H_6$. Summing C and H and taking the ratio of H over C yields a value of about 1.82. $R_{HC}$ (exhaust) is assumed to be about 2.33, since it is assumed that the hydrocarbons in the exhaust will be about 100 percent hexane, $C_6H_{14}$. Thus, it is apparent that, using the appropriate assumptions, there will be a substantial difference between $R_{HCF}$ and $R_{HC}$. Use of assumptions varying from the assumptions $R_{HCF}$=1.82 and $R_{HC}$=2.33 described above is within the scope of the invention. For example, the assumed value for $R_{HCF}$ may be in a range of about 1.7 to about 2.0, while the assumed value for $R_{HC}$ may be in a range of about 2.1 to about 2.5. (Note that for natural gas fuel ($CH_4$), both $R_{HCF}$ and $R_{HC}$ would be about 4.) One of ordinary skill in the art will be able to determine other suitable ratios based upon the composition of fuel, in view of the present discussion.

In view of the conservation of carbon, hydrogen, and oxygen in the above combustion reaction, there can be developed 3 equations and 3 unknowns. These equations are shown for the conservation of oxygen (2), conservation of carbon (3), and conservation of hydrogen (4), respectively:

$$2n = 2k + 1 + k' \quad (2)$$

$$1 = k + 1 + m \quad (3)$$

$$R_{HCF} = mR_{HC} + 2k' \quad (4)$$

The following equations illustrate the ratios $CO/CO_2$ ($R_{CO/CO2}$) and $HC/CO_2$ ($R_{HC/CO2}$) of the exhaust, in view of equation 1 above:

$$[CO]/[CO_2] \equiv R_{CO/CO_2} = 1/k \quad (5)$$

$$[CH_{R_{HC}}]/[CO_2] \equiv R_{HC/CO_2} = m/k \quad (6)$$

By rearranging the above equations, they can be solved by substitution, as shown below. Initially, substituting equations 5 and 6 into equation 3:

$$1 = k + k \times R_{CO/CO_2} + k \times R_{HC/CO_2} = k(1 + R_{CO/CO_2} + R_{HC/CO_2}) \quad (7)$$

$$k_{CO_2} \equiv k = \frac{1}{(1 + R_{CO/CO_2} + R_{HC/CO_2})} \quad (8)$$

Substituting equation 6 into equation 4 provides:

$$R_{HCF} = mR_{HC} + 2k' = kR_{HC/CO_2} \times R_{HC} + 2k' \quad (9)$$

Rearranging the above equation provides:

$$k'_{H_2O} \equiv k' = \frac{1}{2}(R_{HCF} - kR_{HC/CO_2} \times R_{HC}) \quad (10)$$

Substituting equation 10 and equation 5 into equation 2:

$$2n = 2k + kR_{CO/CO_2} + k' \quad (11)$$

$$2n = 2k + kR_{CO/CO_2} + \frac{1}{2}(R_{HCF} - kR_{HC/CO_2} \times R_{HC}) \quad (12)$$

$$n_{O_2} \equiv n = \frac{k}{2}\left[2 + R_{CO/CO_2} - \frac{R_{HC/CO_2} \times R_{HC}}{2}\right] + \frac{R_{HCF}}{4} \quad (13)$$

$$n_{O_2} \equiv n = \frac{k}{2}\left[2 + R_{CO/CO_2} - \frac{R_{HC/CO_2} \times R_{HC}}{2}\right] + \frac{R_{HCF}}{4} \quad (13)$$

From equations 8 and 6:

$$m_{HC} \equiv m = \frac{R_{HC/CO_2}}{(1 + R_{CO/CO_2} + R_{HC/CO_2})} \quad (14)$$

From equations 8 and 5:

$$l_{CO} \equiv l = \frac{R_{CO/CO_2}}{(1 + R_{CO/CO_2} + R_{HC/CO_2})} \quad (15)$$

A first calculation provides the percent concentration of $CO_2$ in the tailpipe of the vehicle for a wet exhaust gas (i.e., including water vapor):

$$\% CO_2 = \frac{k_{CO_2}}{k_{CO_2} + l_{CO} + m_{CH} + k'_{H_2O} + 3.76 n_{O_2}} \quad (16)$$

Rearranging the above equation 16 provides:

$$\% CO_2 + \frac{1}{1 + \frac{l_{CO}}{k_{CO_2}} + \frac{m_{CH}}{k_{CO_2}} + \frac{k'_{H_2O}}{k_{CO_2}} + \frac{3.76 n_{O_2}}{k_{CO_2}}} \quad (17)$$

From equation 5 and equation 6:

$$\frac{l_{CO}}{k_{CO_2}} = R_{CO/CO_2} \text{ and } \frac{m_{CH}}{k_{CO_2}} = R_{HC/CO_2} \quad (18)$$

From equations 8, 10, and 13, the following equations are derived:

$$\frac{k' H_2O}{k_{CO_2}} = \frac{R_{HCF}}{2}(1 + R_{CO/CO_2} + R_{HC/CO_2}) - \frac{R_{HC}}{2} R_{HC/CO_2} \quad (19)$$

$$\frac{3.76 n_{O_2}}{k_{CO_2}} = \frac{3.76 R_{HCF}}{4}(1 + R_{CO/CO_2} + R_{HC/CO_2}) + \frac{3.76}{4}(4 + 2R_{CO/CO_2} - R_{HC/CO_2} \times R_{HC}) \quad (20)$$

Combining terms, the following equation is provided:

$$\% CO_2^{-1} = 1 + R_{CO/CO_2} + R_{HC/CO_2} + \frac{5.76 R_{HCF}}{4}(1 + R_{CO/CO_2} + \quad (21)$$

-continued $$R_{HC/CO_2}) + \frac{3.76}{4} \left( 4 + 2R_{CO/CO_2} - \frac{5.76}{4} R_{HC/CO_2} \times R_{HC} \right)$$

Combining like terms, there is provided the following equation:

$$\% CO_2^{-1} = 4.76 + \frac{5.76 R_{HCF}}{4} + R_{CO/CO_2} \left( 1 + \frac{5.76 R_{HCF}}{4} + \frac{3.76 \times 2}{4} \right) + R_{HC/CO_2} \left( 1 + \frac{5.76 R_{HC}}{4} - \frac{5.76}{4} R_{HC} \right) \quad (22)$$

As described above, based on an assumption of $R_{HCF}$=1.85 and $R_{HC}$=2.33, the following equation is solved for the concentration of carbon dioxide. This equation is utilized in the determination of carbon monoxide content based upon wet exhaust gas:

$$[CO_2] = \frac{1}{7.42 + 5.54 R_{CO/CO_2} + 0.308 R_{HC/CO_2}} \quad (23)$$

According to a second calculation, in order to solve for dry exhaust gas (i.e., excluding water vapor), the term k' (the number of moles of water in the exhaust) is omitted from equation 17 above:

$$\% CO_2 = \frac{1}{1 + \frac{l_{CO}}{k_{CO_2}} + \frac{m_{CH}}{k_{CO_2}} + \frac{3.76 n_{O_2}}{k_{CO_2}}} \quad (24)$$

$$\% CO_2^{-1} = 1 + R_{CO/CO_2} + R_{HC/CO_2} + \frac{3.76 R_{HCF}}{4} (1 + R_{CO/CO_2} + R_{HC/CO_2}) + \frac{3.76}{4} (4 + 2R_{CO/CO_2} - R_{HC/CO_2} \times R_{HC}) \quad (25)$$

Combining terms:

$$\% CO_2^{-1} = 4.76 + \frac{3.76 R_{HCF}}{4} + R_{CO/CO_2} \left( 1 + \frac{3.76 R_{HCF}}{4} + \frac{7.52}{4} \right) + R_{HC/CO_2} \left( 1 + \frac{3.76 R_{HCF}}{4} - \frac{3.76 R_{HC}}{4} \right) \quad (26)$$

As described above, based on an assumption of $R_{HCF}$=1.85 and $R_{HC}$=2.33, for dry exhaust gas:

$$\% CO_2^{-1} = 6.53 + 4.62 R_{CO/CO_2} + 0.549 R_{HC/CO2} \quad (27)$$

To summarize, considering the molar amounts of the components in the combustion reaction (equation 1 above), the concentration of carbon dioxide based upon dry exhaust is shown in the equation below:

$$[CO_2] = \frac{k_{CO_2}}{k_{CO_2} + l_{CO} + m_{CH_{RHC}} + 3.76 n_{IATM} + O_{H_2O}} \quad (28)$$

Similar to equations 16 and 28, the following equation describes the concentration of carbon dioxide based upon wet exhaust (i.e., including water vapor in the exhaust).

$$[CO_2] = \frac{k_{CO_2}}{k_{CO_2} + l_{CO} + m_{CH_{RHC}} + 3.76 n_{IATM} + k'_{H_2O}} \quad (29)$$

In view of the above derivation, the following equation can be used to calculate carbon dioxide concentration based upon dry exhaust:

$$[CO_2] = \frac{1}{6.53 + 4.62 R_{CO/CO_2} + 0.549 R_{HC/CO_2}} \quad (27)$$

Similar to equation 27 above, in view of the above derivation, the following equation can be used to calculate carbon dioxide concentration based upon wet exhaust:

$$[CO_2] = \frac{1}{7.42 + 5.54 R_{CO/CO_2} + 0.308 R_{HC/CO_2}} \quad (23)$$

Inasmuch as the factors including $R_{HC/CO2}$ make a negligible contribution to the accuracy of the carbon dioxide calculation in equations 27 and 23, the $CO_2$ concentration is in practice calculated according to the following equations. Equation 30 is utilized for calculation of $CO_2$ concentration based upon dry exhaust, while equation 31 is utilized for calculation of $CO_2$ concentration based upon wet exhaust.

$$[CO_2] = \frac{1}{6.53 + 4.62 R_{CO/CO_2}} \quad (30)$$

$$[CO_2] = \frac{1}{7.42 + 5.54 R_{CO/CO_2}} \quad (31)$$

Because $R_{CO/CO2}$ is defined as the concentration of carbon monoxide divided by the concentration of carbon dioxide:

$$[CO] = R_{CO/CO_2} \times [CO_2] \quad (32)$$

The values for $R_{CO/CO2}$ and $R_{HC/CO2}$ are substituted in equation 30 above to provide an estimated concentration of carbon monoxide in the exhaust plume. This value is multiplied by the calculation of carbon dioxide content given by equation 30 (dry exhaust) or equation 31 (wet exhaust) to provide the carbon monoxide content of the exhaust. Thus, the invention provides the option of calculating carbon monoxide content based upon either dry or wet exhaust, depending upon the standard values to which the content is compared in determining whether the tested vehicle is excessively polluting.

In this manner, the percentages of carbon monoxide and carbon dioxide in the exhaust can be determined from the slope of (a) a line that can be plotted as a calibrated CO value versus a calibrated $CO_2$ value and (b) a line that can be plotted as a calibrated HC value versus a calibrated $CO_2$ value.

Hydrocarbon Measurement

The hydrocarbon content of the exhaust plume is preferably measured in accordance with the method described below.

An initial step of the analysis includes the determination of a correlation between the concentration of hydrocarbons (HC) and carbon dioxide ($CO_2$) to provide the relative molar amounts of hydrocarbons and carbon dioxide in the exhaust plume. As described above, this correlation can be obtained by plotting in a correlation graph the HC and $CO_2$ values obtained by the data processor 25 via the detectors 17, as described above, to provide a HC:$CO_2$ molar ratio (also represented by $R_{HC/CO2}$ or HC/$CO_2$).

The analysis for calculation of hydrocarbon content of the exhaust also should include the use of an average measurement of typical carbon dioxide concentrations obtained from measurements of exhausts of hundreds or thousands of motor vehicles operated in or near the locale in which the remote test is being performed. Preferably, the assumed carbon dioxide concentration is obtained from data compiled from local inspection and maintenance (I/M) programs sponsored by a governmental agency. Alternatively, this assumed concentration could be determined experimentally by the operator of the invention prior to performance of the remote testing.

The carbon dioxide content of exhaust produced by an internal combustion engine of a moving motor vehicle is generally in a range of about 12 volume percent or molar percent to about 18 volume percent or molar percent. The predetermined carbon dioxide content estimation, as indicated above, is based generally on experience obtained in I/M programs.

More specifically, the concentration of carbon dioxide in the exhaust plume of a motor vehicle will generally be in a range of about 14 volume percent to about 16 volume percent, and more particularly about 15 volume percent (e.g., about 15.3 percent), based upon the dry volume of the total exhaust gas (i.e., excluding water vapor). The concentration of carbon dioxide will typically be in a range of about 12 volume percent to about 14 volume percent, and more particularly about 13 volume percent (e.g., about 13.4 volume percent) based upon the wet volume of the exhaust gas (i.e., including water vapor).

This predetermined carbon dioxide value will vary depending upon the locality in which the remote test is performed. The general values described above may be influenced, for example, by the ambient temperature, the ambient pressure (based on altitude, for example), and other factors.

Using the aforementioned ratio of hydrocarbon to carbon dioxide that is described above, the concentration of the hydrocarbons can then be calculated from the general measurement of $CO_2$. An analog or digital multiplier, preferably a part of, or associated with, the data processor 25, multiplies the ratio of $HC:CO_2$ by the predetermined typical concentration of carbon dioxide in the exhaust plume.

For example, assuming that the carbon dioxide concentration criterion is taken to be 15%, then the concentration of hydrocarbons (in volume or molar percent) in the exhaust plume would be calculated according to the following equation:

$$\%HC = 15\% \times HC/CO_2 \tag{33}$$

Prior methods for using infrared absorption data to determine hydrocarbon content of the exhaust gas typically have caused an under-reporting of the hydrocarbon content. There typically are many species of hydrocarbons in the exhaust plume, and in order to simplify the apparatus, it is assumed that all of these species absorb infrared light at a relatively few wavelengths, thereby causing an under-reporting of the hydrocarbon content. The present invention addresses this problem by preferably using an experimentally determined correction factor to compensate for any undermeasurement. Preferably, the %HC measured in equation 33 above is multiplied by this correction factor to provide a final measurement of hydrocarbon concentration.

For cars, this correction factor is preferably in a range of about 1.5 to about 4, more preferably in a range of about 1.7 to about 2.7, and most preferably about 2.2. For light trucks, the correction factor is preferably in a range of about 1.5 to about 4, more preferably in a range of about 1.8 to about 3.4, and most preferably about 2.6. Preferably, the apparatus described above is programmable based upon local conditions. In this manner, the apparatus of the invention can provide data that are directly comparable to data obtained through typical I/M programs that utilize flame ionization techniques for the measurement of hydrocarbons. An article relevant to such correction factors by Singer et al., "A Fuel-Based Motor Vehicle Emission Inventory," *Journal of the Air & Waste Management Association*, Vol. 46, No. 6 (June 1996) is hereby incorporated herein by reference it its entirety.

In accordance with another embodiment of the invention, the CO concentration can be calculated in a manner similar to that used for the calculation of hydrocarbons. In this embodiment, the correlation between CO and $CO_2$ is calculated in the manner described above. The typical level of carbon dioxide content is then multiplied by the ratio of carbon monoxide to carbon dioxide. For example, assuming the concentration of carbon dioxide to be 15%, the carbon monoxide content (in volume or molar percent) could be estimated according to the following equation:

$$\%CO = 15\% \times CO/CO_2. \tag{34}$$

Measurement of Oxides of Nitrogen

According to another feature of the invention, the concentration of oxides of nitrogen ($NO_x$, such as NO) in the exhaust plume can be measured.

The first factor used in the calculation of the concentration of NO is a ratio of $NO/CO_2$ ($R_{NO/CO2}$), which is obtained from the data provided by the detectors 17 and data processor 25. The data representing the measurement of the relative molar amounts of nitrogen oxide and carbon dioxide is used to derive the molar ratio of nitrogen oxide to carbon dioxide ($NO/CO_2$), as described above for the ratios of $HC/CO_2$ and $CO/CO_2$.

The second factor used in the calculation of the NO concentration is the $CO_2$ content in the exhaust plume. For the calculation of NO concentration, the $CO_2$ concentration is obtained by using the estimation of $CO_2$, described above, preferably obtained by measuring the $CO_2$ content of the exhaust of a large number of vehicles. Alternatively, the method described above for obtaining the $CO_2$ content in the measurement of carbon monoxide could be utilized.

The concentration of NO is determined by multiplying the concentration of carbon dioxide by the ratio of $NO/CO_2$ ($R_{NC/CO2}$) in the exhaust plume, as shown in the following equation:

$$\%NO = [CO_2] \times NO/CO_2 \tag{35}$$

Solid particulate matter emitted from exhaust systems may also be a matter of concern, and the system and method of the present invention can also be adapted to measure the opacity of the exhaust of a vehicle. In this manner, there can be provided an indication of the non-gaseous particulate matter being generated by the vehicle engine. The method and apparatus of the invention could also be adapted to measure the mass emissions of a motor vehicle (e.g., in grams per mile) by incorporating a general assessment of the vehicle's fuel economy.

The method of the invention is simplified from prior methods in that there is no requirement to measure an absolute amount of carbon dioxide in the exhaust plume through the use of a full array of infrared beams. This simplifies the required apparatus and infrared absorption calculations.

In addition, unlike some prior approaches, the method and apparatus of the invention do not require use of an erroneous assumption that the fuel and the exhaust have the same empirical composition, in order to measure the carbon monoxide content of the exhaust. The invention provides an accurate, yet still simple, manner of measuring the carbon monoxide content. In addition, the invention does not require an assumption that the hydrocarbon content of the exhaust is negligible, as in other prior methods.

Moreover, in measuring the hydrocarbon content of the exhaust, the chemical composition of the fuel and the stoichiometry of its composition are not relied upon as part of the calculation. Unlike prior approaches, calculation of hydrocarbon concentration will be based neither on assumptions about the chemical composition of the fuel nor on the stoichiometric ratios associated with combustion of the fuel.

The inventive method is also advantageous in that for the measurement of hydrocarbon content it does not require an erroneous assumption that the fuel and the exhaust have the same empirical composition, as required in at least one other prior method, and yet has the advantage of improved simplicity. Prior assumptions about the hydrocarbon content of the exhaust are particularly inappropriate because there are upwards of one hundred hydrocarbon species that may be included in automobile exhaust, many of which may have different infrared absorption spectra. As a consequence, the prior art inevitably underestimates the hydrocarbon content of the exhaust. The present invention addresses this problem by preferably using a correction factor to compensate for any inevitable undermeasurement as described above.

The method of the invention is still further advantageous because it does not require the use of ultraviolet radiation to measure $NO_x$ pollutants. In addition, the $NO_x$ content can be measured in the relatively simple manner described above.

What is claimed is:

1. An apparatus for sensing a composition of an exhaust plume, comprising:
    a light source that radiates an infrared light beam through said plume, said beam including a plurality of predetermined wavelengths;
    a detector that detects said beam passing through said plume at said predetermined wavelengths, wherein a first of said predetermined wavelengths is associated with carbon dioxide and a second of said predetermined wavelengths is associated with a second gas;
    means for computing a ratio of said second gas to carbon dioxide based upon said first and second detected wavelengths; and
    a multiplier that multiplies said ratio by a predetermined estimation of a concentration of carbon dioxide in said plume, to provide a measurement of a concentration of said second gas.

2. The apparatus of claim 1, wherein:
    said second gas is a hydrocarbon.
3. The apparatus of claim 1, wherein:
    said second gas is carbon monoxide.
4. The apparatus of claim 1, wherein:
    said second gas is an oxide of nitrogen.
5. The apparatus of claim 1, wherein:
    said second gas is nitric oxide.
6. The apparatus of claim 1, wherein:
    said predetermined estimation of carbon dioxide is in a range of about 13 percent to about 18 percent based upon the volume of the plume.
7. The apparatus of claim 1, wherein:
    said predetermined estimation of carbon dioxide is in a range of about 14 percent to about 16 percent based upon the dry volume of the plume.
8. The apparatus of claim 1, wherein:
    said predetermined estimation of carbon dioxide is in a range of about 12 percent to about 14 percent based upon the wet volume of the plume.
9. The apparatus of claim 1, wherein:
    said detector comprises a plurality of photodetectors, each photodetector being sensitive to a band of wavelengths that includes only one of said predetermined wavelengths.

10. The apparatus of claim 1, wherein each detector comprises a photosensitive element and a filter disposed between said plume and the photosensitive element having a passband coinciding with a respective band of wavelengths.
11. The apparatus of claim 1, wherein said predetermined estimation of a concentration of carbon dioxide is experimentally obtained.
12. The apparatus of claim 1, wherein said second gas is a hydrocarbon, further comprising:
    a multiplier that multiplies said measurement of concentration of hydrocarbon by an experimentally determined factor.
13. The apparatus of claim 1, wherein said second gas is a hydrocarbon and a third of said predetermined wavelengths is associated with nitrogen oxide, further comprising:
    means for computing a ratio ($R_{NO/CO_2}$) of said nitrogen oxide to carbon dioxide based upon said first and third detected wavelengths; and
    a multiplier that multiplies said ratio ($R_{NO/CO_2}$) by said predetermined estimation of a concentration of carbon dioxide in said plume, to provide a measurement of a concentration of said nitrogen oxide.
14. The apparatus of claim 1, wherein said exhaust plume is produced by burning a fuel and wherein said second gas is a hydrocarbon and a third of said predetermined wavelengths is associated with carbon monoxide, further comprising:
    means for computing a second ratio ($R_{CO/CO_2}$) of carbon monoxide to carbon dioxide based upon said first and third detected wavelengths; and
    means for computing a concentration of said carbon monoxide in said plume from said first ratio and said second ratio ($R_{CO/CO_2}$) based upon an assumption of a first C:H ratio of fuel and a second C:H ratio of the exhaust plume, said first and second C:H ratios being different.
15. The apparatus of claim 14, wherein:
    said first C:H ratio is about 1.85 and said second C:H ratio is about 2.33.
16. A method of sensing a composition of an exhaust plume from a moving vehicle, comprising the steps of:
    radiating an infrared light beam through said plume, said beam including a plurality of predetermined wavelengths;
    detecting said beam passing through said plume at said predetermined wavelengths, wherein a first of said predetermined wavelengths is associated with carbon dioxide and a second of said predetermined wavelengths is associated with a second gas;
    computing a ratio of said second gas to carbon dioxide based upon said first and second detected wavelengths; and
    multiplying said ratio by a predetermined estimation of a concentration of carbon dioxide in said plume, to provide a measurement of the concentration of said second gas.
17. The method of claim 16, wherein:
    said second gas is carbon monoxide.
18. The method of claim 16, wherein:
    said second gas is a hydrocarbon.
19. The method of claim 16, wherein said second gas is a hydrocarbon, further comprising:
    multiplying said measurement of concentration of hydrocarbon by an experimentally determined factor.

20. The method of claim 16, wherein:
said second gas is an oxide of nitrogen.
21. The method of claim 16, wherein:
said second gas is water vapor.
22. The method of claim 16, wherein:
said predetermined estimation is in a range of about 13 percent to about 18 percent based upon the volume of the exhaust plume.
23. The method of claim 16, wherein:
said predetermined estimation is in a range of about 14 percent to about 16 percent based upon the dry volume of the exhaust plume.
24. The method of claim 16, wherein:
said predetermined estimation is in a range of about 12 percent to about 14 percent based upon the wet volume of the exhaust plume.

* * * * *